(12) United States Patent
Keeble et al.

(10) Patent No.: US 7,837,724 B2
(45) Date of Patent: Nov. 23, 2010

(54) CONTROL DEVICE FOR MEDICAL CATHETERS

(75) Inventors: Duncan R. Keeble, Oxfordshire (GB); Anthony Jones, Oxfordshire (GB); Peter W. Phillips, Oxfordshire (GB)

(73) Assignee: Anson Medical Ltd. (GB)

( * ) Notice: Subject to any disclaimer, the term of this patent is extended or adjusted under 35 U.S.C. 154(b) by 1413 days.

(21) Appl. No.: 10/504,245

(22) PCT Filed: Feb. 11, 2003

(86) PCT No.: PCT/GB03/00646

§ 371 (c)(1), (2), (4) Date: May 19, 2005

(87) PCT Pub. No.: WO03/068302

PCT Pub. Date: Aug. 21, 2003

(65) Prior Publication Data

US 2005/0228475 A1     Oct. 13, 2005

(30) Foreign Application Priority Data

Feb. 11, 2002 (GB) ................. 0203177.1

(51) Int. Cl.
*A61F 2/06* (2006.01)
(52) U.S. Cl. .................. 623/1.11; 623/1.12
(58) Field of Classification Search ........ 623/1.11, 623/1.12, 1.23; 222/159; 606/108, 114, 606/127, 200; 401/65, 68, 74, 77, 78
See application file for complete search history.

(56) References Cited

U.S. PATENT DOCUMENTS

| | | | | |
|---|---|---|---|---|
| 1,695,625 | A | * | 12/1928 | Wild ...................... 401/74 |
| 5,038,967 | A | * | 8/1991 | Braun ..................... 222/519 |
| 5,433,723 | A | | 7/1995 | Lindenberg et al. |
| 5,707,376 | A | | 1/1998 | Kavteladze et al. |
| 5,776,142 | A | * | 7/1998 | Gunderson ............ 623/1.11 |
| 5,891,154 | A | | 4/1999 | Loeffler |
| 2003/0199966 | A1 | * | 10/2003 | Shiu et al. ............. 623/1.12 |

FOREIGN PATENT DOCUMENTS

| | | |
|---|---|---|
| JP | 02-182268 | 7/1990 |
| JP | 05-200121 | 8/1993 |
| JP | 07-293658 | 11/1995 |
| JP | 11-089942 | 4/1999 |

* cited by examiner

*Primary Examiner*—Todd E Manahan
*Assistant Examiner*—Jonathan A Hollm
(74) *Attorney, Agent, or Firm*—Craig A. Fieschko, Esq.; DeWitt Ross & Stevens S.C.

(57) ABSTRACT

A control mechanism comprises an elongate handle 10 having an external thread 12 and a barrel 20 with internally projecting pins 21 threaded over handle 10. Rotation of barrel 20 causes handle 10 to move back and forth along its longitudinal axis to retract and advance a catheter sheath to which handle 10 is coupled, thereby enabling an implant to be deployed by the catheter. Rotation movement of barrel 20 and longitudinal movement of handle 10 can be disassociated to enable speedy retraction or advancement of the catheter sheath.

16 Claims, 3 Drawing Sheets

CONTROL DEVICE FOR MEDICAL CATHETERS

FIELD OF THE INVENTION

The present disclosure relates to an improved mechanism for controlling medical catheters and more particularly those catheters which are used to deliver implants to particular sites within a patient's body, such as cardiovascular stents. The system has applications in a wide range of catheter or laparoscopic surgery and is of particular value in delivering larger implants, such as stent grafts, within arteries.

BACKGROUND OF THE INVENTION

Catheter delivery systems usually comprise a sheath at whose tip is contained the device to be implanted. The device is usually highly compressed, particularly in diameter, and the device is released by drawing the sheath back, allowing the device to emerge from its tip. All designs feature a structure which provides a reaction force for the device so that it maintains its position while the sheath is being withdrawn.

A simple example of this type of delivery system is provided with the Talent™ stent-graft manufactured by Medtronic, Inc. The system suffers two principal draw-backs. The first is that the highly compressed implant pushes against the wall of the sheath with such force that withdrawing the sheath also requires a considerable force. A second (allied) problem is that providing the necessary force to deploy the stent-graft can be difficult for the medical practitioner to achieve with accuracy or control, allowing the implant to be deployed too quickly and, potentially, displaced from its intended landing site.

An improved system has been incorporated into the delivery system supplied with the AneuRx™ stent-graft, also manufactured by Medtronic. In this system, a barrel-shaped component of the handle of the delivery system is rotated and acts on a lead-screw to withdraw the sheath with both mechanical advantage and precision.

Additional complexity is added in this system because the sheath stretches significantly while it is being withdrawn. When the medical practitioner's hand is being repositioned on the barrel of the handle, the barrel is free to rotate and is prone to spin back as the sheath springs back to its original length. The AneuRx™ system therefore employs a conventional ratchet mechanism on the rotating barrel to prevent this elastic recoil.

Introduction of the ratchet incurs a further complexity. When the delivery catheter is being withdrawn from the patient, it is highly desirable that the sheath be slid back into its original position to cover the remaining internal components of the delivery system so that they do not inflict any trauma onto the viscera of the patient. For this purpose, the AneuRx system employs a separate control to override the ratchet and allow the barrel to be rotated in the opposite sense to allow the sheath to be returned to its starting position.

SUMMARY OF THE INVENTION

The present invention performs similar functions to the AneuRx system but employs fewer components, allowing it to be fabricated more cheaply, operated more simply and for the mechanism to have greater reliability.

According to a first aspect of the present invention, there is provided a control mechanism for retraction and advancement of a sheath at the end of a delivery catheter, comprising a first part which is able to move back and forth along a longitudinal axis, said first part being associated with the catheter sheath so that movement of said first part in one direction along said axis causes retraction of the sheath and movement in the opposite direction causes advancement of the sheath, a second part which can be rotated about a rotation axis, movement of said first and second parts being associated whereby rotation of said second part causes said first part to move along said longitudinal axis to retract or advance the catheter sheath depending on the direction of said rotation, wherein movement of said first and second parts can be disassociated to allow movement of said first part to advance the sheath without corresponding rotation of said second part.

The invention preferably employs a rotatable barrel on the handle of the delivery system, said barrel being connected permanently to a tubular sheath which is used to contain the implant during insertion into the patient. The rotatable barrel has a first threaded feature on at least one of its cylindrical surfaces which engages a second threaded feature on the handle of the delivery system so that when rotated, the barrel moves axially along the said handle. An alternative embodiment can be constructed in which the rotatable barrel is held axially captive and its threaded feature engages a second threaded feature on an additional component which is itself connected permanently to the sheath and moves axially along the handle as the barrel is rotated, moving the sheath into or out of the handle.

A preferred feature of the present invention is a modification to the first or second threaded component. The modification allows the diameter of the threaded component to be increased if it is an outer thread, or to be decreased if it is an internal thread, beyond a point where the first threaded component no longer engages the second threaded component. The modification allows the rotatable barrel to have two modes of operation: the first operating mode occurs when the first and second threaded components are engaged, the barrel is rotated and operates the lead screw to provide mechanical advantage and a slow controlled release. The second operating mode occurs when the first and second threaded components have been adjusted so that they cannot engage and the rotatable barrel can be slid axially, without mechanical advantage but at higher speed. The first operating mode is optimum for releasing the implant while the second operating mode is more suitable for returning the sheath to its starting position, or for deploying a second, less critical component of the implant.

An improvement to this basic system includes provision for the diameter of at least one threaded component to be adjusted by at least one feature on the thread or handle. In this case, the threaded parts can be disengaged when the said feature or features are reached at a point or points along the thread. Thus the lead-screw action can be engineered to be effective over a defined length or lengths while permitting the second mode of operation over the remaining length or lengths.

A further improvement in the basic system can be achieved if the modified threaded component is stable in both the engaged or disengaged states. This allows the mechanism to employ the mechanical advantage of the lead-screw, but once disengaged to return over the threaded part as a simple sliding movement. This feature allows the rapid return of the sheath to the starting position.

An additional improvement to at least one of the threaded components involves introducing discontinuities into the thread so that tension in the sheath will not encourage the rotatable barrel to spin when it is released. Various discontinuous features can be included ranging between a random roughening of the profile of the thread which increases friction between the first and second threaded components to a 'staircase' type feature in the thread so that it has alternating stationary and advancing components along its length. It will be understood that recoil in the sheath will cause the barrel to return along the length of an advancing part of the thread but to remain stationary when a stationary component of the thread has been reached.

In all cases, benefit can be derived from the use of multiple or 'multi-start' threads in this mechanism.

In a practical embodiment of the invention, the handle of the catheter system is threaded over part of its surface with a multi-start thread. A rotatable barrel with a smooth inner surface is free to slide over the threaded handle. The barrel is provided with a number of short cylindrical pins which are radially arranged to pass through the wall of the barrel. Preferably, where a multi-start thread is employed, at least one radially arranged pin is employed to engage with each separate thread. The pins can slide in the wall of the barrel and their length is arranged such that when in a first position, they project maximally into the barrel and the pins engage the thread of the handle. Thus the pins form the first threaded component referred to above and the threaded handle comprises the second threaded component. In a second position, the pins can be pushed outwards through the wall of the barrel so that they no longer engage the thread of the handle, allowing the barrel to move freely over the threaded handle.

The fit of the pins in the wall of the barrel and the selection of materials can be made such that the pins can be held firmly in either the said first or the said second positions. Practical materials for the barrel include polyester and the pins can be suitably manufactured from 316 stainless steel.

Conveniently, the pins can be moved from the said first position to the said second position by decreasing the depth of the thread cut into the handle or by providing a raised component over which the pins are made to pass. Advantageously, the diameter of the pins is increased at one end, said end lying inside the rotatable barrel. This feature prevents the pin from falling out of the barrel, while the length of the pin is such that the body of the handle passing through the rotatable barrel will prevent the pin from falling through the wall of the barrel into the handle.

Typically, the handle has a diameter of 10 to 40 mm although systems with handles as small as 3 mm in diameter and as large as 150 mm in diameter could usefully be made. Considering a typical system with a handle of 25 mm diameter, the thread depth is conveniently 2 mm±1 mm with a pitch of 20 mm±10 mm per turn. The rotatable barrel is conveniently between 30 mm and 100 mm long while its wall thickness is 4 mm±2 mm. The internal diameter of the rotatable barrel is ideally less than 1 mm larger than the outer diameter of the threaded part of the handle. The pins which comprise the first threaded component are 2 mm±1 mm in diameter and have an overall length which is approximately the sum of the wall thickness of the barrel plus the depth of the thread plus half the clearance between the internal diameter of the rotatable barrel and the outer diameter of the threaded part of the handle. Those skilled in the art will appreciate that the many combinations of dimensions can be chosen which will provide a functioning system and that final selection will depend upon ease and reproducibility of manufacture as well as the ergonomics of the system for the user. When designing larger or smaller systems, the basic dimensions for the 25 mm system should be scaled as appropriate and then adjusted for ergonomics and ease of manufacture.

BRIEF DESCRIPTION OF THE DRAWINGS

A number of preferred embodiments of the present invention will now be described with reference to the drawings, in which:—

DETAILED DESCRIPTION OF PREFERRED VERSIONS OF THE INVENTION

Figure 1:
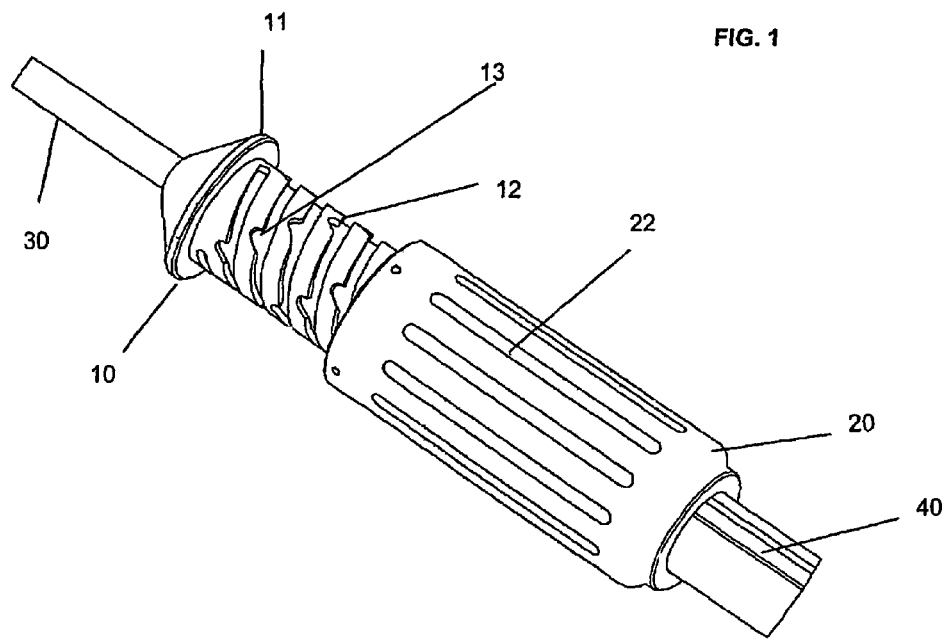
FIG. 1 shows a perspective view of a control mechanism in accordance with the present invention.

The control mechanism comprises a handle (10) which is an elongate element with a central bore (14) through which delivery catheter (30) can pass. The outside surface of handle (10) has thread (12) with a plurality of steps (13) therein and a stop (11) at one end of handle (10).

Barrel (20) has four pins (21) projecting from its inner surface, pins (21) engaging with thread (12) to enable barrel (20) to be threaded axially over the external surface of handle (10).

The external surface of barrel (20) has a hand grip (22) to enable the user to grip barrel (20) and rotate it about handle (10).

Pins (21) are mounted in four holes (not shown) in barrel (20) and are able to move radially from a position of maximum projection into the centre of barrel (20) to a position of radial retraction and minimal projection into the centre of barrel (20). This enables pins (21) to engage and disengage with thread (12) as will be described below.

Catheter delivery tube (40) is disposed in the bore of handle (10) at the end distal to stop (11) and positioned coaxially with handle bore (14) such that catheter (30) can be threaded through catheter delivery tube (40) and bore (14) to emerge as shown in FIG. 1.

Figure 2A:
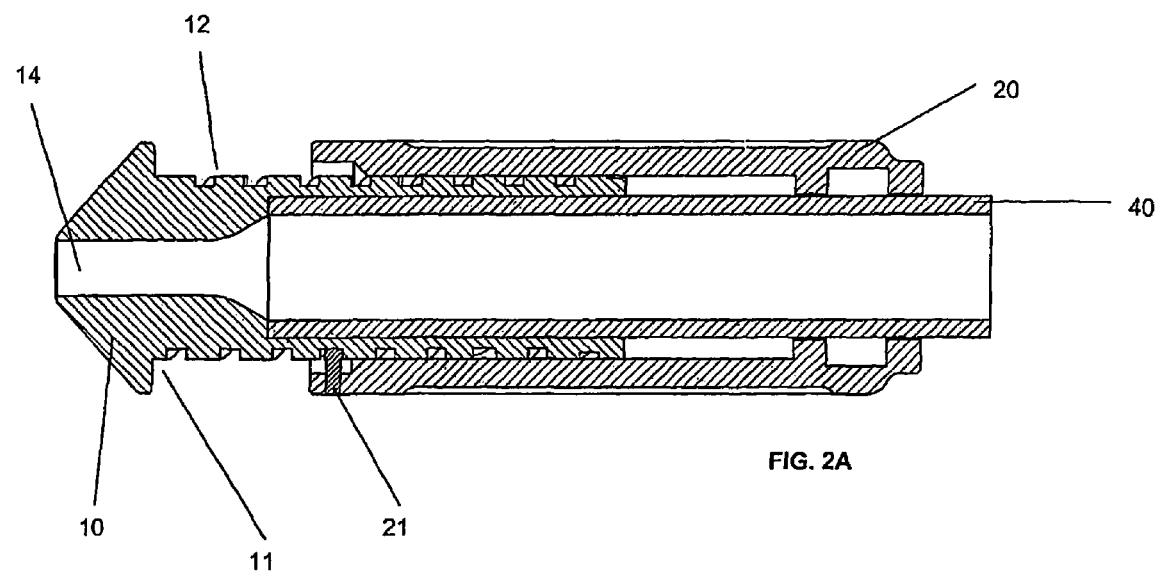
FIG. 2A shows a cross-sectional view of the control mechanism at FIG. 1.
Figure 2B:
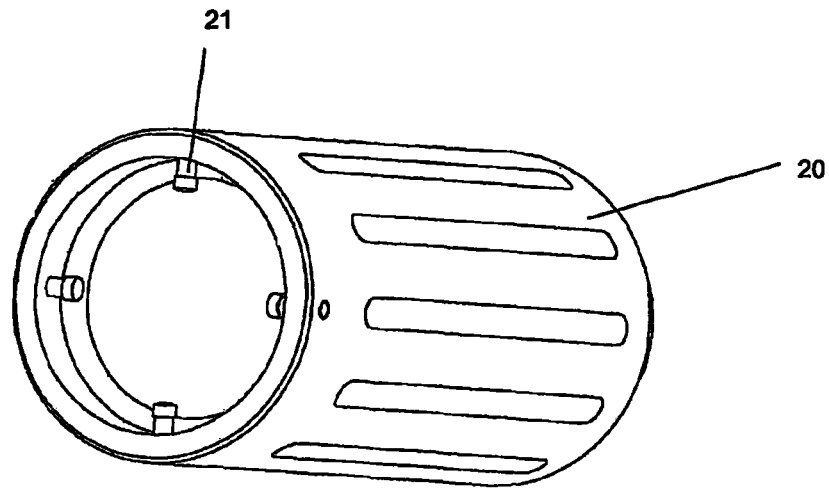
FIG. 2B shows a perspective view of the barrel of FIG. 2A shown separately from the rest of the components.
Figure 3A:
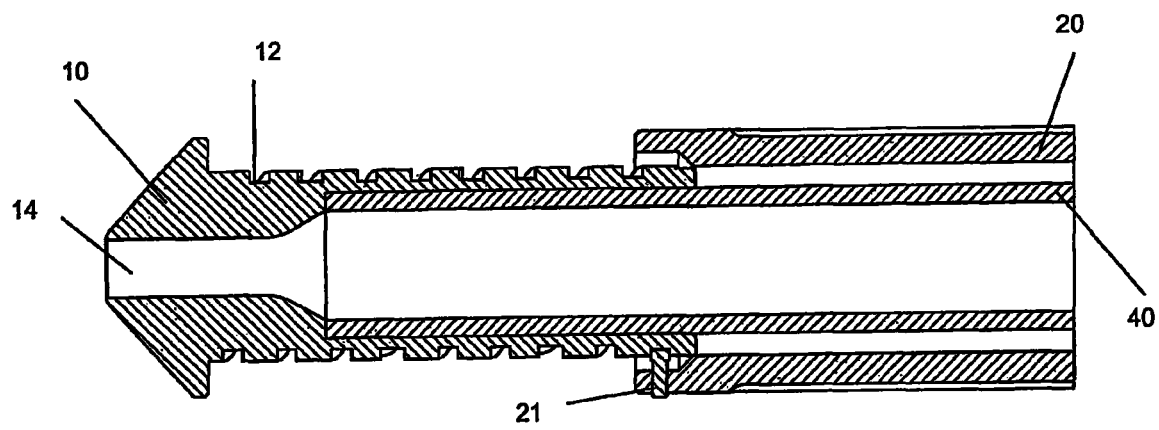
FIG. 3A is a cross-sectional view of a control mechanism in accordance with the invention in a different position to that shown in FIG. 2A.
Figure 3B:
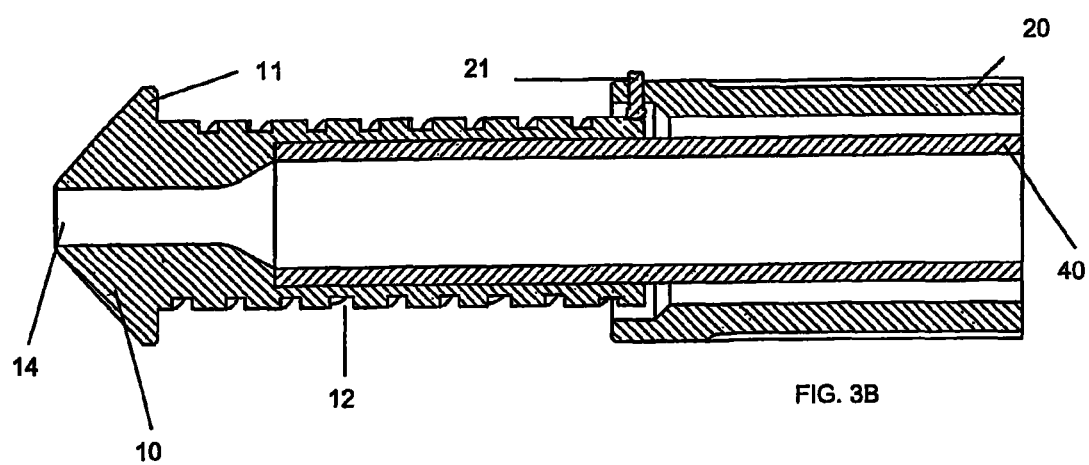
FIG. 3B is a cross-sectional view of a control mechanism in accordance with the invention in a different position to that shown in FIGS. 2A and 3A.
Figure 4A:
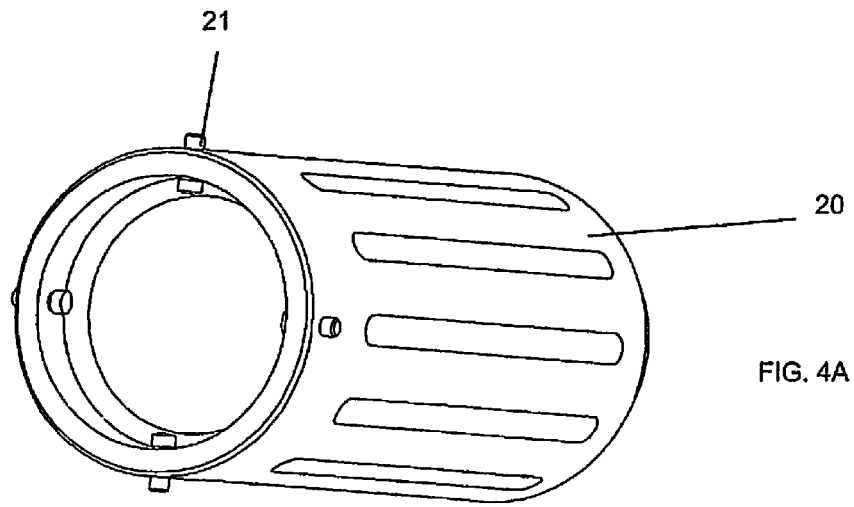
FIG. 4A is a perspective view of the barrel of the control mechanism of FIG. 4B shown separately from the rest of the components.
Figure 4B:
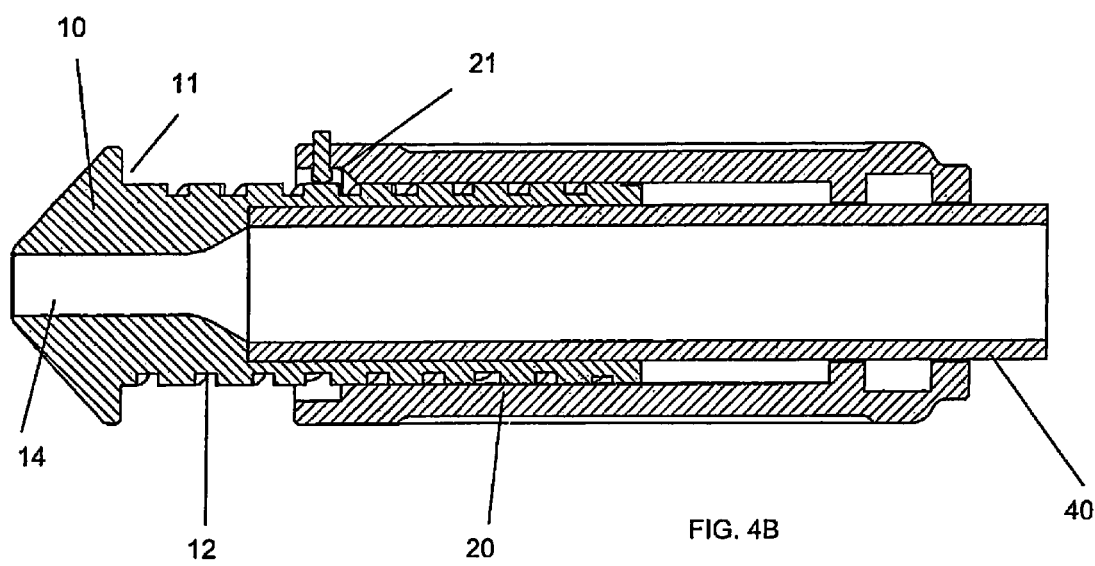
FIG. 4B is a cross-sectional view of a control mechanism in accordance with the invention shown in a different position to that of FIGS. 2A, 3A and 3B.

FIGS. 2A and 2B, 3A and 3B and 4A and 4B show pins (21) in states of increasing disengagement from thread (12), that is from a state in which pins (21) project radially into the centre of barrel (20) in FIGS. 2A and 2B to a state in which pins (21) are retracted into barrel (20) and thereby disengaged from thread (12) (FIGS. 4A and 4B) with FIGS. 3A and 3B showing state of partial disengagement.

In use, barrel (20) is rotated anticlockwise about the longitudinal axis of handle (10) with pins (21) engaging in thread (12) as shown in FIG. 2A. This rotational movement causes pins (21) to move down thread (12) away from stop (11), thereby causing longitudinal movement of barrel (20) away from stop (11) down thread (12).

Coupling between barrel (20) and the distal end of catheter (30) (not shown) causes the sheath at said distal end to retract, thereby baring the end of catheter (30) and delivering the device to be implanted from catheter (30).

If the user releases barrel (20) then elastic recoil of the catheter sheath will cause rotation of barrel (20) in a clockwise sense. However, pins (21) will quickly become lodged in steps (13), thereby preventing further clockwise rotation of barrel (20) and preventing advancement of the catheter sheath.

As barrel (20) is rotated further, pins (21) reach the end of thread (12) distal from stop (11). Pins (21) then ride up a ramp (not shown) at the end of thread (12) which urges pins (21) radially outwardly to retract into barrel (20). FIG. 3A shows a single pin (21) beginning to disengage and FIG. 3B shows said pin almost fully disengaged. When pins (21) are fully disengaged from thread (11), handle (20) can be moved axially towards stop (11) without the need for rotation of barrel (20). This thereby allows advancement of the catheter sheath to re-cover the end of catheter (30).

In an alternative embodiment, continuing longitudinal movement of barrel (20) away from stop (11) without the need for continuing anti-clockwise rotation of barrel (20) is possible once pins (21) have reached the end of thread (12). The user can thereby withdraw the catheter sheath completely by fast longitudinal separation of barrel (20) and handle (10) with the more controlled rotational separation being reserved for the first part of the separation.

Once the implant has been delivered from the catheter, the user can advance the catheter sheath by moving barrel (20) towards handle (10) longitudinally without the need for rotational movement of barrel (20). As pins (21) reach the end of handle (10) distal from stop (11) a ramp on handle (10) may be provided to urge pins (21) to retract into barrel (20) and allow continuing longitudinal movement without the need for rotation of barrel (20) with respect to handle (10).

The invention claimed is:

1. A catheter sheath with a sheath control mechanism for retraction and advancement of the sheath, the control mechanism having:
   a. a first part which is able to move back and forth along a longitudinal axis, the first part being associated with the catheter sheath so that movement of the first part in one direction along the axis causes retraction of the sheath and movement in the opposite direction causes advancement of the sheath,
   b. a second part which can be rotated about a rotation axis, wherein:
   (1) the movement of the first and second parts is associated by a thread disposed on one of the first and second parts, the other of the first and second parts having a lug which is able to move into and out of the thread, whereby rotation of the second part causes the first part to move along a longitudinal axis to retract or advance the catheter sheath depending on the direction of the rotation,
   (2) the lug is disengageable to disassociate the movement of the first and second parts, thereby allowing movement of the first part to advance the sheath without corresponding rotation of the second part, and
   (3) the one of the first and second parts having the thread disposed thereon has a ramp, up which the lug moves on rotation of the second part, the ramp urging the lug out of the thread to thereby disengage the lug from the thread.

2. The control mechanism of claim 1, wherein the first part is an elongate element and the second part is a sleeve which fits over the elongate element.

3. The control mechanism of claim 1, wherein the longitudinal movement of the first part beyond an end of the thread distal to the catheter sheath causes disassociation of the movement of the first and second parts.

4. The control mechanism of claim 1, wherein the ramp is disposed at an end of the thread.

5. The control mechanism of claim 1, additionally comprising means for preventing free rotation of the second part in such a manner as to allow advancement of the sheath.

6. The control mechanism of claim 5, wherein the means for preventing comprises an abutment surface in the thread.

7. A catheter sheath with a sheath control mechanism for retraction and advancement of the sheath, the control mechanism having:
   a. an elongate element which is able to move back and forth along a longitudinal axis, the elongate element being associated with the catheter sheath so that movement of the elongate element in one direction along the axis causes retraction of the sheath and movement in the opposite direction causes advancement of the sheath,
   b. a sleeve which can be rotated about a rotation axis, wherein:
   (1) the elongate element and sleeve are associated by a thread and a member engaging the thread, whereby rotation of the sleeve causes the elongate element to move along the longitudinal axis to retract or advance the catheter sheath depending on the direction of the rotation,
   (2) the thread has steps indented therein, the steps:
      (a) being spaced along the thread, and
      (b) each extending at least partially in a longitudinal direction,
      wherein the member restrains relative rotation of the elongate element and sleeve in at least one of the clockwise and counterclockwise directions if the member is urged into one of the steps, and
   (3) the thread can be disengaged from the member to allow movement of the elongate element to advance the sheath without corresponding rotation of the sleeve, and
   (4) the thread has a ramp, up which the member moves upon relative rotation of the sleeve and elongate element, the ramp urging the member out of the thread in order to disengage the member from the thread.

8. The control mechanism of claim 7 wherein the member is movable in an at least partially radial direction to disengage from the thread.

9. The control mechanism of claim 7 wherein each step is bounded by opposing sides spaced circumferentially along the thread, one of the sides being ramped such that when the member is within one of the steps, relative rotation of the elongate element and sleeve in one of the clockwise and counterclockwise directions drives the member up the ramp of the step.

10. The control mechanism of claim 7 wherein the ramp is disposed at an end of the thread.

11. The control mechanism of claim 1 wherein the thread has steps depressed therein, the steps:
   a. being spaced along the thread, and
   b. each extending at least partially in a longitudinal direction,
wherein the lug restrains relative rotation of the first and second parts in at least one of the clockwise and counterclockwise directions if the lug is urged into one of the steps.

12. The control mechanism of claim 11 wherein each step is bounded by opposing sides spaced circumferentially along the thread, one of the sides being ramped such that when the lug is within one of the steps, relative rotation of the elongate element and sleeve in one of the clockwise and counterclockwise directions drives the lug up the ramp of the step.

13. A catheter sheath with a sheath control mechanism for retraction and advancement of the sheath, the control mechanism having:
   a. a first part which is able to move back and forth along a longitudinal axis, the first part being associated with the catheter sheath so that movement of the first part in one direction along the axis causes retraction of the sheath and movement of the first part in the opposite direction along the axis causes advancement of the sheath,
   b. a second part which can be rotated about a rotation axis,
wherein:
   (1) one of the first and second parts bears:
      (a) threading extending along a length parallel to the longitudinal axis, and
      (b) a ramp with height varying in a radial direction,
   (2) the other of the first and second parts bears a member which is movable in an at least partially radial direction to engage and disengage the threading, and
   (3) upon relative rotation of the first and second parts, the ramp urges the member radially out of the thread in order to disengage the member from the thread,
whereby:
   i. the member can engage the threading to rotatably associate the first and second parts, whereby rotation of the second part causes the first part to move along the longitudinal axis, and
   ii. the member can disengage the threading to disassociate the first and second parts, whereby at least one of the first and second parts can move longitudinally with respect to the other part without relative rotation between the parts.

14. The control mechanism of claim 13 wherein the ramp is disposed at an end of the thread.

15. The control mechanism of claim 13 wherein the thread has steps indented therein, the steps:
   a. being spaced circumferentially along the thread, and
   b. each extending at least partially in a longitudinal direction,
wherein the member restrains relative rotation of the first and second parts in at least one of the clockwise and counterclockwise directions when the member rests within one of the steps.

16. The control mechanism of claim 15 wherein each step is bounded by opposing sides spaced circumferentially along the thread, one of the sides being ramped such that when the member is within one of the steps, relative rotation of the elongate element and sleeve in one of the clockwise and counterclockwise directions drives the member up the ramp of the step.

* * * * *